United States Patent [19]

Keller et al.

[11] Patent Number: 5,130,149
[45] Date of Patent: Jul. 14, 1992

[54] PROCESS FOR THE MANUFACTURE OF NOVEL COFFEE FLAVORANTS

[75] Inventors: Alfred Keller, Zurich; Victor Krasnobajew, Küsnacht; Juan-Ramon Mor, Zurich; Rudolf Steiner, Bassersdorf, all of Switzerland

[73] Assignee: Givaudan Corporation, Clifton, N.J.

[21] Appl. No.: 259,552

[22] Filed: Oct. 18, 1988

Related U.S. Application Data

[63] Continuation of Ser. No. 908,698, filed as PCT/CH85/00181, Dec. 24, 1985, abandoned.

[30] Foreign Application Priority Data

Jan. 10, 1985 [CH]  Switzerland ............... 96/85
Dec. 13, 1985 [CH]  Switzerland ............ 5331/85

[51] Int. Cl.⁵ ............................................. A23L 1/234
[52] U.S. Cl. ...................... 426/46; 426/533; 426/650
[58] Field of Search ............... 426/533, 46, 650

[56] References Cited

U.S. PATENT DOCUMENTS

| | | | |
|---|---|---|---|
| 2,835,592 | 5/1958 | Rusoff | 426/533 X |
| 3,102,815 | 9/1963 | Spotholz et al. | 426/533 |
| 3,102,817 | 9/1963 | Green | 426/533 |
| 3,689,277 | 9/1972 | Sfat et al. | 426/533 X |
| 4,187,324 | 2/1980 | Shirbroun | |

FOREIGN PATENT DOCUMENTS

| | | |
|---|---|---|
| 1206821 | 2/1960 | France . |
| 2046076 | 11/1980 | United Kingdom . |

OTHER PUBLICATIONS

"Ullmanns Encyklopaedie der technischen Chemie", Verlag Chemie, Weinheim, 1977, 4, Band 13; 429-440.

*Primary Examiner*—Joseph Golian
*Attorney, Agent, or Firm*—Robert F. Tavares; Linda A. Vag

[57] ABSTRACT

A process for the manufacture of coffee flavoring substances is described; this process comprises enzymatically proteolyzing soya meal, heating the proteolyzate and isolating the resulting water-soluble material from the reaction mixture. Furthermore, there are described; flavoring substance compositions which contain these novel coffee flavoring substances, foodstuffs and semi-luxury consumable which contain such coffee flavoring substances or flavoring substance compositions, and the use of the novel flavoring substance compositions or coffee flavoring substances for the flavoring of foodstuffs and semi-luxury consumables or as coffee substitutes.

15 Claims, No Drawings

PROCESS FOR THE MANUFACTURE OF NOVEL COFFEE FLAVORANTS

This application is a continuation of application Ser. No. 06/908,698, filed as PCT/CH85/00181, Dec. 24, 1985, now abandoned.

It is known that coffee substitutes (coffee surrogates) and coffee additives (coffee spices) can be manufactured by roasting natural plant parts (e.g. up to temperatures of 180-240° C.) (Ullmanns Encyklopadie der technischen Chemie, Verlag Chemie, Weinheim, 4th edition volume 13. (1977). pages 429-440). These surrogates yield coffee-like drinks with hot water. The coffee additives are likewise obtained by roasting plant parts as well as sugar-containing raw materials. Roots, fruits and seeds are suitable raw materials. Examples are barley rye, chicory sugar beet figs carob beans, groundnut kernels, soya beans, almonds and dehulled acorns. The coffee substitute mixtures are commercialized as powders. Not one of the mixtures which has hitherto become known in this respect has, however, been capable of wholly satisfying organoleptically. In particular, the genuine coffee character is lacking olfactorily and gustatorily in the mixtures, and the strength of flavour can likewise often leave much to be desired. In this respect, the more recent pertinent processes, described hereinafter in more detail, also bring about no improvement.

In this respect, there have now been found products which are not accompanied by these disadvantages. As the raw material source for these novel substances there is used soya meal, namely soya meal which is de-fatted (as much as possible), from which the novel coffee flavouring substances are obtainable according to a novel process.

The invention is accordingly concerned with a process for the manufacture of novel coffee flavouring substances, which process comprises enzymatically proteolyzing soya meal, heating the proteolyzate and isolating the resulting water-soluble material from the reaction mixture. Furthermore, the invention is concerned with flavouring substance compositions which contain these novel coffee flavouring substances, with foodstuffs and semi-luxury consumables ("Genussmittel"; ("Genussmittel") which contain such coffee flavouring substances or flavouring substance compositions, with the use of the novel flavouring substance compositions or coffee flavouring substances for the flavouring of foodstuffs and semi-luxury comsumables or as coffee substitutes.

The manufacture of soya meal and its de-fatting, for example with hexane, is described e.g. in J. Schorrmuller, Kohlenhydratreiche Lebensmittel, Springer-Verlag Berlin (1967). 395 seq. or in Food Technology, Oct. 1982, 122, 123.

As the soya meal there is preferably used the product of [largely]de-fatted soya beans ground as finely as possible [this allows the enzymes good access to the soya proteins], e.g. of the quality Soyafluff W 200 from the firm Central Soja, Indiana IL. This material is "not toasted". However, "toasted" material, e.g. material from ESO-Chemie (Hamburg) or from Stern-Chemie (Hamburg) can also be used.

The enzymatic proteolysis can be carried out with usual proteolytically-active enzymes (proteases). As proteases there are sutiable: proteases of vegetable origin (e.g. ficin, bromelain, papain), of animal origin (e.g. trypsin [for toasted meal: the trypsin inhibitor present in non-toasted meal is no longer active in this case], chymotrypsin) or of microbial origin (e.g. Rhozym, e.g. type P-53 or P-41, from Genencor Inc., Corning N.Y.) or Neutrase (from Novo Industri, Bagsvaerd, Denmark), which enzymes proteolyze aqueous suspensions of soya products in a relatively short time, i.e. are capable of breaking down the soya proteins to peptides and amino acids relatively rapidly. Proteases of microbial origin are especially suitable because with them a particularly good coffee flavour is achieved in the present case.

A compilation of the usual proteolytically active ferments (enzymes) is found, for example in Tony Godfrey and Jon Reichelt, Industrial Enzymology, The Application of Enzymes in Industry. The Nature press and McMillan Publ. Ltd. (1983) 466 seq. und in Gerald Reed Enzymes in Food Processing, Academic Press NY and London. (1966). 148 seq.

A suitable enzyme concentration can be determined readily by a sensoric experiment and conveniently amounts to about 0.1-1 wt.% of enzyme based on the amount of soya meal. On economic grounds the incubation time should not be too long. It should as a rule determined under the conditions given hereinafter, not exceed about 1-24 hours. The determination itself is carried out according to usual methods for the determination of soluble proteins, see e.g. Methods in Food Analysis, 2nd ed. Maynard A. Joslyn, Academic Press (1970), 630 seq., i.e. for example by measuring the optical density: for this purpose samples are removed from the reaction mixture at regular time intervals, these are treated with 15% trichloroacetic acid, insoluble material is centrifuged off and the optical density of the solution is measured at 280 nm. The reaction can be considered to have finished for the present purpose when a significant increase of the optical density can no longer be ascertained At this point in time the incubation is conveniently discontinued.

The substrate concentration [i.e. the concentration of the dry starting material]can be quite high: it lies e.g. at about 20 to about 50 wt.%. The PH value of the medium conveniently lies between 5-7, preferably around about 6.5 to about 7; but the incubation can also be carried out in a weakly acidic medium, e.g. at pH 5, or in a weakly alkaline medium. e.g. at pH 7.5.

The suitable incubation temperature lies in the range of about 30 to 60° C. especially 50 to 60° C. When commercial proteases are used the proteolysis is generally terminated after a few hours. e.g. 5 to 24 hours.

As stated above, the suitable substrate concentration generally lies at about 20 to about 50 wt.%. In the case of Soyafluff and soya meals having similar specifications, it conveniently amounts, for example, to about 20 to about 30% (w/v). The upper limit follows from practical considerations: the formation of lumps should not occur during the enzymolysis.

In accordance with the invention the pre-treated soya meal, namely the aqueous roteolyzate is now heated.

The pre-treated soya meal is a yellowish to brownish concentrate. It can be used for the (further) heating directly in the form of this concentrate, e.g. an about 20-30% concentrate, as the reaction product of the enzymatic proteolysis. Accordingly, it need not be separated after the proteolysis, which permits an extremely rational production.

The desired flavour forms in the present case when the enzymatically-pretreated soya meal is heated to temperatures which are usual in the case of the known non-enzymatic browning reaction, the classical Maillard reaction [i.e. reaction of amino acids with sugars or peptide or protein fragments with sugars see e.g. Food Res. 25, (1960), 491–594, and also Römpps Chemie-Lexikon, volume 4, pages 2464/2465, 8th edition Franckh'sche Verlagshandlung Stuttgart (1985)], thus, for example, to temperatures of 140° to 200° C. in particular to about 140° C. to 180° C., especially to about 170° C. The pressure conveniently amounts to about 10–30 bar, especially about 15–20 bar.

The heating time is normally inversely proportional to the temperature; it conveniently amounts to about ½ to 5 hours.

After completion of the reaction the products obtainable in accordance with the invention are conveniently separated from the remaining particles, especially the (reaction) products (of the Maillard reaction) which are insoluble in water: it has been shown that the insoluble particles have a negative influence especially on the quality of the flavour. The separation of the insoluble particles is conveniently carried out by filtration or centrifugation.

Isolation, filtration or separation is carried out e.g. with the aid of pressure filters (batchwise or continuous operation), suction filters, decanters, microfilters or ultrafilters e.g. from the firm Westfalia or Alfa-Laval, or by means of centrifuges e.g. bucket centrifuges or drop-bottom bucket centrifuges. The filter cake is thereupon conveniently again suspended in water in order to produce additional water-soluble material. The combined filtrates or centrifugates are then concentrated e.g. by means of plate evaporators or rotation evaporators, conveniently to a concentration of 50–75° Brix, or pulverized. The pulverizate is conveniently produced by spray-drying, vacuum-drying, freeze-drying (lyophilization) or drum-drying.

The products obtainable in accordance with the invention, namely the products of a defined enzymatic hydrolysis (a proteolysis) and a browning reaction, are now surprisingly highly concentrated coffee flavouring substances which can be diluted or distributed in edible materials in a manner known per se. They can be converted according to methods known per se into the usual forms of use such as solutions, pastes or powders. As carrier materials there come into consideration e.g.: gum arabic or, preferably, maltodextrins. In other respects, the formulation of such flavours as well as the flavouring of foodstuffs can be carried out in a manner known per se (see J. Merory; Food flavourings, Composition, manufacture and use; Avi Publ. Co., Westport 1968).

The following Table contains details concerning suitable concentration ranges for various application forms of the flavours obtainable in accordance with the invention in flavouring substance compositions:

| Application form | General | Preferred |
|---|---|---|
| | [Percentage content of the flavour manufactured in accordance with the invention (in weight %) in the desired composition] | |
| Solutions | 1–100% | 10–60% |
| Pastes | 1–100% | 10–90% |
| Spray-dried powder | 3–100% | 15–85% |
| Lyophilized vacuum-dried powder | 2–100% | 8–18% |

The flavouring substance compositions in accordance with the invention can be used, for example in the manufacture or flavouring of various products from the range of foodstuffs, convenience foods, instant products, semi-luxury consumables and of flavours.

Examples are: coffee, coffee essence, powdered coffee, coffee surrogate (coffee substitute), coffee liquor, baked goods such as cakes, biscuits, waffle fillings, dessert powders, ice cream, chocolate, fillings for filled chocolate, praline fillings, chocolate powder couverture coatings, butter icing marzipan, mixed milk products, milky foods, cocoa powder, cocoa powder-containing preparations, coffee flavours, nut flavours, nougat flavours, caramel flavours etc.

Examples of convenient concentration ranges (in weight percentages) of the flavours in accordance with the invention for various uses are:

| | General | Preferred |
|---|---|---|
| Instant coffee (e.g. an instant coffee mixture: flavour in accordance with the invention/conventional instant coffee = 1:1) | 0.1–1.5% | 0.3–1% |
| Chocolate | 0.1–1.5% | 0.3–1% |
| Waffle filling | 0.5–1.0% | about 1% |
| Finished dessert | 0.5–1.0% | about 1% |
| Yoghurt | 0.1–1.0% | 0.6–0.8% |
| Ice cream | 0.5–1.0% | about 1% |

From this it is evident that the convenient concentration of the products in accordance with invention corresponds approximately to the concentration of conventional soluble coffee powder.

The products obtainable in accordance with the invention can be used as complete coffee substitutes or, however, preferably for the improvement, modification or intensification of the flavour of coffee products and coffee flavours. In this way a variation in type can be produced in a simple manner by mixing products in normal commercial use with any amounts, in the case of instant coffee referably up to about 50% (g/g). of the products obtainable in accordance with the invention.

The amount of the flavouring substances in accordance with the invention in the flavoured product can generally amount to approximately 0 05 to approximately 10%, preferably approximately 0.1 to 4%.

As far as the flavour character is concerned, the following applies:

The higher the temperature and the longer the duration of the Maillard reaction, the typical strongly aromatic roast note of genuine coffee comes more to the forefront. Where, on the other hand, milder notes are desired, lower temperatures and shorter reaction times suggest themselves.

EXAMPLE

Enzymolysis 349.5 1 of water are added to a clean autoclave and heated to 50–55° C. There is added thereto while stirring well 0.5 kg of Rhozym P-53 [or 0.5 kg of Neutrase], and thereupon 150 kg of soya meal (Soyafluff W-200 from the firm Central Soya, Fort Wayne IN) are added. In order to prevent the formation of lumps, the addition of the soya meal extends over 30 minutes. Thereupon, the reaction mixture is held at 50° C. for 16 hours while stirring well.

The enzymolysis can be carried out analogously using proteases of vegetable or animal origin. In these cases the temperature and PH data provided by the individual manufacturers are to be observed or the corresponding data in the technical literature are to be observed.

Browning reaction

The autoclave is firstly heated up to 90–95° C. within one hour by means of steam of 6 bar. Thereupon it is heated to 168–170° C. by means of steam of 20 bar within about 1½ hours. This temperature is maintained, for a product having a strong roast note, for e.g. 3 hours and the progress of the browning reaction is checked by sampling and sensoric testing at each complete hour. The internal pressure rises to about 25 bar during the browning reaction. In order to maintain a constant pressure the pressure valve can be adjusted to a value of about 10–15 bar. After completion of the browning reaction the mixture is cooled rapidly to 50° C. and the reaction mixture is removed from the autoclave with the aid of the residual pressure.

Working-up

The 470 kg of crude biobase is separated in lots in a Ferrum drop-bottom bucket centrifuge [Ferrum AG, CH 5102 Rupperswil]at 800 g [it can, however, also be isolated via a pressure filter, decanter or separator].

After centrifugation of 4 lots (about 100 l of crude material) the centrifuge cake is washed with 20 litres of water and kept. In this manner there are obtained 360 litres of filtrate and 100 kg of moist filter cake. The filter cake is suspended in 200 l of water while stirring vigorously. It is again centrifuged and the yield now amounts to 200 l of filtrate and 95 kg of filter cake (49% dry material). The combined filtrates )560 litres) have a concentration of 75.6 kg of dry material (13.5° Brix; determination by means of an aerometer or refractomer). Concentration is carried out continuously at 25 millibar and 45–48° C. using an APV-plate evaporator [Ott AG, CH-3076 Worb]. There are obtained 115.7 kg of a viscous syrup which contains 63% of dry material; yield 77.1% (based on the soya meal used). The syrup obtained (65% Brix) can be
a) used directly for flavouring purposes, or
b) used for the manufacture of solutions and pastes, or
c) dried to powders.

Flavouring

A palatable milky coffee is produced by adding a lyophilized powder (LP) in a concentration of 0.3%–0.5% to milk with a 3% sugar content.

Comparative tests

This water-soluble lyophilized powder was compared sensorically hereinafter with the products of two novel pertinent processes.

A. In accordance with the process of GB-A 2,046,076A (British Soy Product Ltd.) the soya beans are firstly treated with stream before the roasting. Drying, breaking open the shells, roasting and grinding follow. The re-working of Example 1 yields a material which was now compared sensorically with the material LP.

As the crude material there were used:

Soya beans B

Product: BIONA soya beans cultivated biologically
Distributor: MORGA AG, CH 9642 Ebnat-Kappel

Soya beans D

Product: Dr. Dunner's soya beans
Distributor: Die Reformahäuser of Zurich

Soya beans G

Product: Small green soya beans (self-seeding)
Distributor: MORGA AG, CH-9642 Ebnat-Kappel The evaluation was carried out in both cases with 0.1% and 0.2% in 3% sugar water at room temperature.

In the aqueous samples there can indeed be ascertained the coffee, caramel and chocolate notes of the known flavouring substances, but besides also side-notes which clearly influence the flavour, these side-notes being tarry, after stale coffee (ex soya beans D and G), phenolic, slightly tea-like, after tobacco [ashtray smell](ex soya beans B).

It is probably these latter notes which caused the inventor to recommend the replacement of only 2–5% of the caramel, coffee or chocolate flavours of flavoured food-stuffs by the described flavouring substances.

This small concentration is also the greatest disadvantage of the known process as it is uneconomical.

The side-notes probably result from the steam treatment also bringing about a certain thermal decomposition of the proteins, precursors for the Maillard reaction are probably also formed in this case: this swelling and germination of the beans under the mere influence of moisture and the action of heat can, however, never replace a controlled enzymatic hydrolysis of beans which are ground and freed from oil, namely of de-fatted soya meal.

B. In accordance with the process of U.S. Pat. Ser. No. 4,187,324 (Shirbroun) the green soya beans are soaked, comminuted in order to remove the oil, pre-dried, ground, roasted and pulverized.

As starting materials for the re-working there were used the following three sorts of soya beans:
Soya beans B
soya beans D
soya beans G
and finally soya grist SAIS

Product: Soya grist
Distributor: SAIA AG, CH - 6048 Horw
Water content: 10%

The coffee brewed with the product of the re-worked "Example", 0.2% in 3% sugar water, was evaluated as follows.

The individually obtained ground roast products were weighted, treated with 3% sugar water, left to stand at room temperature for 30 minutes and before the evaluation the mixture was filtered through a fluted filter and thus separated from the solid substances still present.

| Sample designation | Description of the flavour |
| --- | --- |
| G | Flavour: white cabbage (sulphurous) vegetable broth, cereal-malty, chocolate |
|   | Odour: white cabbage, vegetable broth |
| B | Flavour: weak, slightly cereal-like, cardboard, paper |
|   | Odour: weak slight roast note |
| D | Flavour: weak, cereal-like, |

| Sample designation | Description of the flavour |
| --- | --- |
| | malty, slightly after caramel, slight roast note |
| | Odour: slightly sooty |
| S | Flavour: weak, cereal-like, malty, aftertaste similar to paper and cardboard |
| | Odour: cereal-like, after rolled oats |

Reference sample

Lyophilized powder LP 0.2% in 3% sugar water at room temperature (an especially well suited method for the accurate investigation of flavour notes):

Flavour: malty, after milk coffee, after biocoffee, "healthy coffee", liquorice in the aftertaste.

Also within the framework of the present investigations studies were of course firstly carried out without the roteolysis step: in this case it was always established that the thus-prepared flavour compositions did not have by far the sought-after typical coffee flavour notes.

On the other hand, the enzymatic treatment of soya meal has, however, hitherto become known especially in the production of HVP hydrolysed vegetable proteins) products. These known products are used primarily for the seasoning of soups and sauces, but there can also be mentioned in this connection a novel soya bean sake, the protein enrichment of soft drinks and special diets in the hospital sector;

see also J. Schormüller, Lehrbuch der Lebensmittelchemie, Springer-Verlag, Berlin (1961). Pages 280-283.

Tony Godfrey, Jon Reichelt, Industrial Enzymology, The Application of Enzymes in Industry, The Nature Press and the McMillan Publ. Ltd., (1983).

Gerald Reed. Enzymes in Food Processing, Academic Press. NY and London. (1966). page 369 and Iida and Sakamoto, Develop. Ind. Microbiology, Vol. 4 (1963). pages 159-165.

We claim:

1. A process for the manufacture of coffee flavouring substances, which process comprises enzymatically proteolyzing soya meal using proteases of microbial origin, in a temperature range of about 30-60° C., heating the proteolyzate to about 140° to about 200° C. and isolating the resulting water-soluble material from the reaction mixture with the aid of pressure filters, suction filters, decanters, microfilters or ultrafilters or by means of centrifuges.

2. A process according to claim 1, wherein
   a) the proteolysis is carried out in a temperature range of about 50-60° C., and,
   b) the proteolyzate is heated to about 140° C. to about 180° C.

3. A process according to claim 2, wherein the isolated material is concentrated to a concentration of 50-75° Brix or is pulverized.

4. A coffee flavouring substance, manufactured according to a process which comprises enzymatically proteolyzing soya meal using proteases of microbial origin, in a temperature range of about 30-60° C., heating the proteolyzate to about 140° to about 200° and isolating the resulting water-soluble material from the reaction mixture with the aid of pressure filters, suction filters, decanters, microfilters or ultrafilters or by means of centrifuges.

5. A flavoring substance composition, which contains a flavouring effective amount of a coffee flavouring substance manufactured according to a process which comprises enzymatically proteolyzing soya meal using proteases of microbial origin, in temperature range of about 30-60° C., heating the proteolyzate to about 140° to about 200° and isolating the resulting water-soluble material from the reaction mixture with the aid of pressure filters, suction filters, decanters, microfilters or ultrafilters by means of centrifuges.

6. A process for the flavouring of foodstuffs and semi-luxury consumables, which process comprises adding thereto a flavouring effective amount of a coffee flavouring substance manufactured according to a process which comprises enzymatically proteolyzing soya meal, using proteases of microbial origin, in a temperature range of about 30-60° C., heating the proteolyzate to about 140° to about 200° and isolating the resulting water-soluble material from the reaction mixture with the aid of pressure filters, suction filters, decanters, microfilters or ultrafilters or by means of centrifuges.

7. Foodstuff or semi-luxury comsumables which contain a flavouring effective amount of coffee flavouring substances manufactured according to a process which comprises enzymatically proteolyzing soya meal using proteases of microbial origin, in temperature range of about 30-60° C., heating the proteolyzate to about 140° to about 200° C. and isolating the resulting water-soluble material from the reaction mixture with the aid of pressure filters, suction filters, decanters, microfilters or ultrafilters or by means of centrifuges.

8. A coffee flavouring substance according to claim 4 wherein
   a) the proteolysis is carried out in a temperature range of about 50-60° C., and,
   b) the proteolyzate is heated to about 140° C. to about 180° C.

9. A coffee flavouring substance according to claim 8 wherein the isolated material is concentrated to a concentration of 50-70° Brix or is pulverized.

10. A flavouring substance composition according to claim 5 wherein
    a) the proteolysis is carried out in a temperature range of about 50-60°, and,
    b) the proteolyzate is heated to about 140° C. to about 180° C.

11. A flavouring substance composition according to claim 10 wherein the isolated material is concentrated to a concentration of 50-75° Brix or is pulverized.

12. A process according to claim 6 wherein
    a) the proteolysis is carried out in a temperature range of about 50-60° C., and
    b) the proteolyzate is heated to about 140° C. to about 180° C.

13. A process according to claim 12 wherein the isolated material is concentrated to a concentration of 50-75° Brix or is pulverized.

14. A foodstuff or semi-luxury consumable according to claim 7 wherein
    a) the proteolysis is carried out in a temperature range of about 50-60° C., and,
    b) the proteolyzate is heated to about 140° C. to about 180° C.

15. A foodstuff or semi-luxury consumable according to claim 14 wherein the isolated material is concentrated to a concentration of 50-75° Brix or is pulverized.

* * * * *